(12) United States Patent
Muir

(10) Patent No.: US 9,572,911 B2
(45) Date of Patent: Feb. 21, 2017

(54) METHOD FOR DECELLULARIZATION OF TISSUE GRAFTS

(71) Applicant: University of Florida Research Foundation, Inc., Gainesville, FL (US)

(72) Inventor: David F. Muir, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

(21) Appl. No.: 14/776,765

(22) PCT Filed: Mar. 17, 2014

(86) PCT No.: PCT/US2014/030688
§ 371 (c)(1),
(2) Date: Sep. 15, 2015

(87) PCT Pub. No.: WO2014/145854
PCT Pub. Date: Sep. 18, 2014

(65) Prior Publication Data
US 2016/0030636 A1 Feb. 4, 2016

Related U.S. Application Data

(60) Provisional application No. 61/794,012, filed on Mar. 15, 2013.

(51) Int. Cl.
*C12N 5/00* (2006.01)
*C12N 5/02* (2006.01)
(Continued)

(52) U.S. Cl.
CPC ........ *A61L 27/3687* (2013.01); *A61L 2430/32* (2013.01)

(58) Field of Classification Search
None
See application file for complete search history.

(56) References Cited

U.S. PATENT DOCUMENTS

| 2005/0043819 A1 | 2/2005 | Schmidt et al. |
| 2010/0028396 A1* | 2/2010 | Ward ............ A61F 2/0059 |
| | | 424/405 |

(Continued)

FOREIGN PATENT DOCUMENTS

CN 101095963 1/2008

OTHER PUBLICATIONS

Thermoscientific, "Thermo Scientific Pierce Cell Lysis Technical Handbook," 2008, pp. 1, 6.

(Continued)

*Primary Examiner* — Chris R Tate
*Assistant Examiner* — Douglas F White
(74) *Attorney, Agent, or Firm* — Saliwanchik Lloyd & Eisenschenk

(57) ABSTRACT

The subject invention pertains to materials and methods for processing tissue to produce a natural, acellular replacement tissue that is immunocompatible with a recipient. According to the subject invention, harvested tissue is subjected to wash solutions wherein only amphoteric detergent(s) are used (e.g., anionic detergents are excluded). Following extraction by amphoteric detergent(s), the tissue is washed with a buffer system to facilitate the clearance of cellular components and detergent. In one embodiment, the subject invention pertains to a replacement tissue that is a nerve graft that supports axonal regeneration, guides axons toward the distal nerve end and/or is immunologically tolerated. Preferably, the nerve graft retains essential extracellular matrix scaffolding as well as biological components that promote nerve regeneration through the nerve graft.

15 Claims, 16 Drawing Sheets

(51) Int. Cl.
*C12P 1/00* (2006.01)
*A61K 35/12* (2015.01)
*A61L 27/36* (2006.01)

(56) References Cited

U.S. PATENT DOCUMENTS

| | | | |
|---|---|---|---|
| 2011/0195107 A1 | 8/2011 | Min et al. | |
| 2013/0224260 A1* | 8/2013 | Ward | A61F 2/0059 424/400 |
| 2014/0257482 A1* | 9/2014 | Ward | A61F 2/0059 623/8 |
| 2014/0335144 A1* | 11/2014 | Ward | A61F 2/0059 424/423 |

OTHER PUBLICATIONS

Moore, A.M. etal., "Acellular nerve allografts in peripheral nerve regeneration: A comparative study," *Muscle & Nerve,* Aug. 2011, (44)2: 221-234.

Kvist, M. et al., "Regeneration in, and properties of, extracted peripheral nerve allografts and xenografts," *Journal of Plastic Surgery and Hand Surgery,* Jun. 2011, 45(3): 122-128.

Ma, X.L. et al., "Biomechanical properties of peripheral nerve after acellular treatment," *Chinese Medical Journal,* Dec. 2011, 124(23): Abstract.

Hudson, Terry W., et al., "Optimized Acellular Nerve Graft is Immunologically Tolerated and Supports Regeneration." *Tissue Engineering,* 2004, 10(11/12): 1641-1651.

Ma, Xin-long et al.,"Biomechanical properties of peripheral nerve after acellular treatment," *Chinese Medical Journal,* Dec. 2011, 124(23): 3925-3929.

\* cited by examiner

METHOD FOR DECELLULARIZATION OF TISSUE GRAFTS

CROSS-REFERENCE TO A RELATED APPLICATIONS

This application is a National Stage Application of International Application No. PCT/US2014/030688, filed Mar. 17, 2014; which claims the benefit of U.S. provisional application Ser. No. 61/794,012, filed Mar. 15, 2013, both of which are incorporated herein by reference in their entirety.

BACKGROUND OF THE INVENTION

Biomedical engineering faces many challenges in the development of tissue that can be used to facilitate healing. For example, a "replacement" tissue should promote tissue regeneration. In doing so, the new tissue must be compatible with the recipient tissue so that neighboring cells accept the replacement. Importantly, the replacement tissue should overcome (or avoid) the immunologic responses typically elicited by the addition of a "foreign body" to a biological system.

Furthermore, the replacement tissue should exhibit the properties and function of the tissue that it is replacing. For example, the replacement tissue should exhibit similar mechanical and structural properties of the original tissue or, at a minimum, not interfere with the native environment. The replacement tissue may act as a scaffold and/or retain biological properties to promote cellular regeneration. Finally, the replacement tissue should not stimulate scar formation that limits tissue regeneration or inhibits the natural function of the underlying tissue.

One particularly challenging embodiment of tissue engineering is the production of nerve grafts that can be used to help regeneration of severed nerves. In direct nerve repair, when the ends of a severed nerve are reconnected (without an interpositional graft), axons will attempt to regrow from the proximal nerve into the distal nerve. In this context, following nerve injury, the distal nerve undergoes a process known as Wallerian degeneration, which involves the breakdown and clearance of nerve elements including the nonfunctional distal axons and their myelin sheaths. In part because of this process, axonal and myelin debris have long been believed to have growth-inhibitory effects that curtail nerve regeneration and may be a mechanical barrier to axonal growth.

Extensive evidence indicates that nerve regeneration is slower when the process of Wallerian degeneration is delayed. Accordingly, it has been widely accepted that the clearance of nerve elements improves axonal growth in the distal nerve. This premise has been extrapolated to nerve grafting and has fostered the belief that cellular debris must also be removed from nerve grafts in order to promote axonal growth. Removal of residual cellular material has also been thought to be necessary to minimize pathogens in the tissue and eliminate immunogenic material that might lead to graft immunorejection. Consequently, processing methods used for nerve grafts have routinely involved rigorous decellularization techniques, even at the expense of disrupting extracellular matrix (ECM) structures and nerve graft integrity that support the regenerative process.

Nerve damage often results in the loss of clean ends for direct repair or a gap created by nerve tissue damage. In this case nerve repair requires the an interpositional graft to bridge the deficit and restore nerve continuity.

For instance, U.S. Pat. No. 7,402,319 (which is incorporated herein in its entirety) describes an acellular nerve allograft that can reinstate nerve continuity and, under the right circumstances, can lead to nerve regeneration. This type of nerve graft is obtained by soaking nerve tissue in several series of solutions with sulfobetaines and anionic surface-active detergents (e.g., Triton X-200), which are used to decellularize the nerve tissue.

Hudson et al. applied a decellularization technique containing Triton X-200™, sulfobetaine-16, and sulfobetaine-10 on rat nerves and reported very high levels of extraction. (Hudson T W, Liu S Y, Schmidt C E. Tissue Eng. 10: 1346-58, 2004). Rodent nerves, however, contain a single nerve bundle (fascicle) and the outer nerve sheaths of rodent nerves have little resemblance to the nerves of larger animals. Most nerves of larger animals (e.g., rabbit, human) have multiple nerve bundles embedded in a collagenous inner epineurium (connective tissue surrounding the nerve bundles). The sheath and intrafascicular structures of human nerves are expansive and have a profound influence on nerve integrity and permeability, including properties that impact tissue extraction. Therefore, knowledge about decellularization and extraction of rodent nerve is at best suggestive of the extraction expected when applied to the nerves from larger animals.

In summary, there remains a need to improve tissue replacements, particularly in the context of nerve tissue. The improved tissue replacement should maintain native structural and bioactive characteristics of the tissue it is replacing, including, for example, laminin activity, and be able to incorporate bioactive compounds or molecules where necessary to promote rapid regeneration, and stimulate tissue repair and regeneration without scarring that can reduce tissue mobility and integrity.

BRIEF SUMMARY OF THE INVENTION

The present invention provides novel methods and compositions for preparing tissue grafts that retain native structure and integrity as well as biological properties required for improved regeneration.

The tissue grafts of the present invention provide a natural replacement tissue or graft that can be obtained via simple preparation steps. The methods of the invention specifically disrupt immunogenic cellular components without significantly altering the natural extracellular structure. Advantageously, the tissue retains biological properties for promoting cellular regeneration through the graft. The native extracellular matrix (ECM) structure is preserved, specifically, in the case of nerve grafts, the basal laminae and endoneurium/endothelial layer retain their natural and generally original structure.

Thus, in one embodiment, the invention provides a nerve graft that supports axonal regeneration, guides the axons toward the distal nerve end and is tolerated immunologically. The acellular nerve graft may be, for example, an isograft, an autograft, an allograft or a xenograft.

In one embodiment, the present invention provides a method for preparing tissue replacement that includes the steps of: washing the replacement tissue, in the absence of any ionic detergents (including any anionic detergent), in a solution comprising at least one amphoteric detergent and then washing the replacement tissue in serial solutions of a buffered salt to remove excess amphoteric detergent. This process is simpler and less expensive than processes of the current art and results in a replacement tissue with better handling properties and with better regeneration-promoting properties.

In a specific embodiment, the amphoteric detergent(s) used according to the subject invention are sulfobetaine-10 (SB-10) and/or sulfobetaine-16 (SB-16).

The present invention also provides a decellularized replacement tissue. In one embodiment, the replacement tissue can form part of a suture, tube, sheet, film, or scaffold for delivery into a recipient. Preferably, the replacement tissue retains biological components that promote regeneration and/or do not elicit immunologic responses following transplantation into the recipient.

In another embodiment, the present invention provides a kit for tissue replacement that comprises a decellularized replacement tissue. The kit may also include one or more solutions useful for re-suspending the replacement tissue of the present invention, e.g., a buffered, sterile saline solution that is pharmacologically acceptable. Furthermore, the kit may also include a vial of solution with cells, or other active agents, that may be added to encourage tissue regeneration (e.g., Schwann cells and/or cytokines). The kit may further include an instruction sheet or booklet that provides the user with detailed instructions for the of the cell-free replacement tissue.

In a specific embodiment, the present invention provides a graft that supports axonal regeneration, guides the axons toward the distal nerve end and is immunologically tolerated. In one example, the graft is a nerve graft. The graft may be frozen prior to decellularization and then stored and shelved for use frozen. Another embodiment is when the nerve graft is prepared for a particular application when freezing preservation is not required; in that case, temperature may be lower or higher depending on the solution in which the graft is stored before use, e.g., including one or more preservative and/or antimicrobial agents.

In one embodiment, a graft that supports regeneration may also include one or more materials that assist in downregulating recipient immune response to graft implantation. For example, a graft of the present invention may include phorbol ester phorbol myristate acetate (PMA) to encourage graft implantation with reduced $CD4^+$ T-cell mediated immune response.

DETAILED DISCLOSURE OF THE INVENTION

Figure 1:
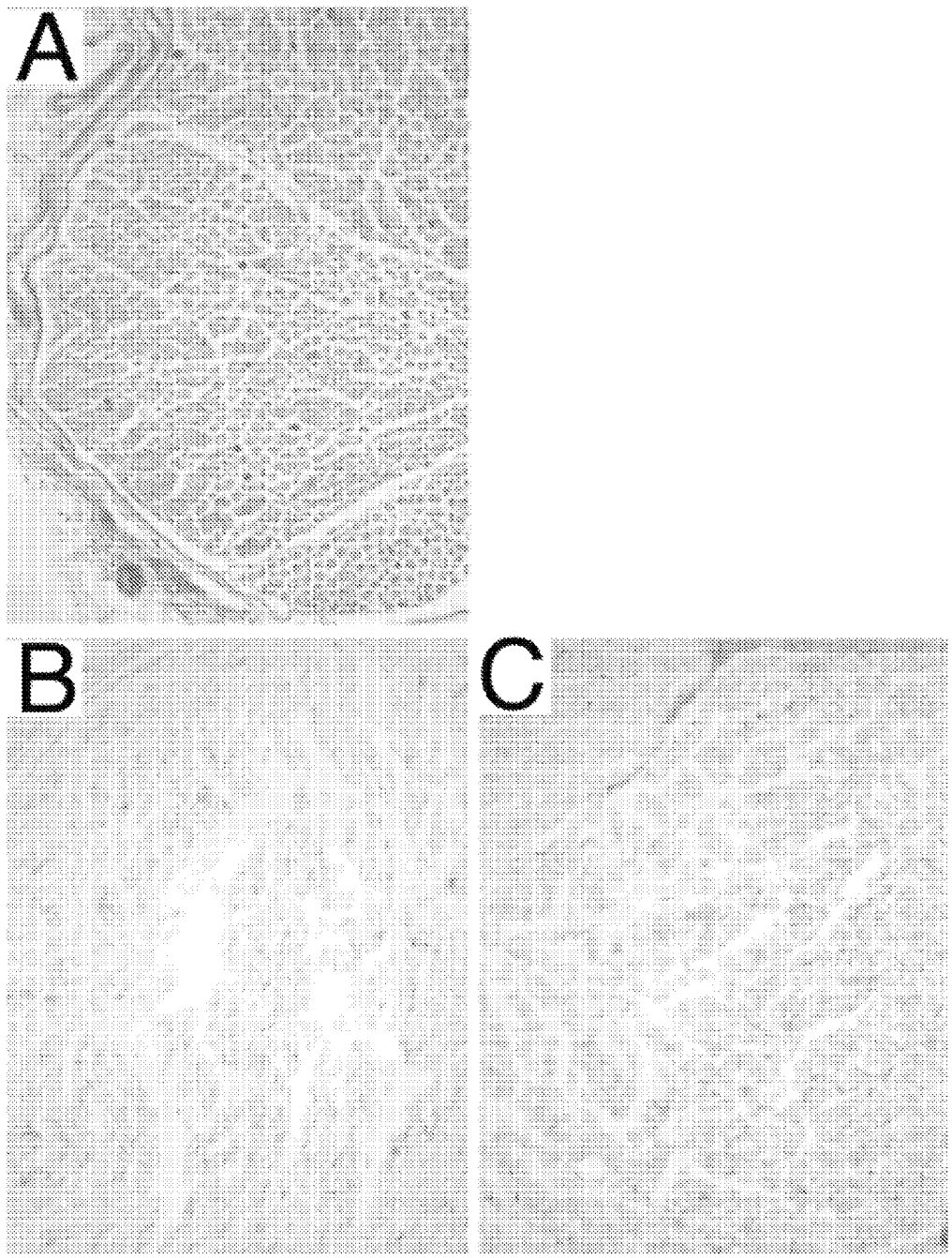
FIG. 1. Hematoxylin and eosin staining of rabbit nerve tissue (control; panel A), rabbit nerve tissue processed in accordance with the process taught by Hudson et al. (DC2; panel B), and rabbit nerve tissue processed in accordance with the method of the subject invention (DC3; panel C).

Terms used herein have meanings as commonly understood by a person of ordinary skill in the fields relevant to the present invention. Terms such as "a," "an," and "the" are not intended to refer to only a singular entity, but include the general class of which a specific example may be used for illustration. The terminology herein is used to describe specific embodiments of the invention, but their usage does not limit the invention, except as outlined in the claims. All technical and scientific terms used herein have the same meaning as commonly understood by one of ordinary skill in the art to which this invention belongs, unless defined otherwise.

In one embodiment, the subject invention provides a nerve allograft that retains the extracellular structure as well as biological properties of peripheral nerve tissue. The allograft is prepared via an improved exclusive decellularization treatment. The decellularization process solubilizes cellular membranes from nerve tissue, thus eliminating the antigens leading to allograft rejection.

The present invention further provides methods for preparing a natural tissue-based graft that is immunologically tolerated and retains the intrinsic structure and architecture of the native tissue. As used herein the term "replacement tissue" is used to describe a tissue that has been removed from a donor animal (live or cadaveric) and that has been treated according to the present invention.

Uses of the grafts in the present invention include but are not limited to: 1) as biocompatible biomaterial that is generally non-immunogenic; 2) as a structural foundation for factors to promote tissue- and recipient-specific, tissue regeneration; and 3) as a research tool to study the recipient response to replacement tissue structure. The present invention also provides a replacement tissue that is generally acellular tissue with processible, biologic, bioactive, and/or biodegradable features.

In accordance with the subject invention it has now been found that, contrary to conventional concerns, the vast majority of residual cellular components in a tissue graft are not problematic; host cells eventually remove them after engraftment. Even residual MHC molecules that could cause rejection are not a problem. To cause a significant immune response MHC components must be retained as closely associated complexes in cell membranes. Since cell membranes and MHC complexes are readily solubilized by mild (non-ionic and amphoteric) detergents according to the subject invention, these concerns are alleviated.

Conventional decellularization technologies require harsh agents and powerful anionic detergents. In accordance with the present invention it has been surprisingly and advantageously determined that extensive cellular extraction is not beneficial, but is, in fact, detrimental, to the engraftment process. Rather, moderate extraction is sufficient to render a tissue allograft immunocompatible and is beneficial for the preservation of the graft ECM required to promote tissue repair.

Unfortunately, washing nerve tissues with ionic detergents (such as Triton X-200™) has been shown to reduce laminin activity. Laminins are major proteins in the basal lamina that are important for tissue regeneration by influencing cell differentiation, migration and adhesion. For example, laminin is a major substrate along which nerve axons grow.

Thus, in accordance with the present invention, mild amphoteric detergents are sufficient to disperse cellular elements sufficiently and simply render a tissue graft immunocompatible, without denaturation of essential intrinsic bioactivities.

DEFINITIONS

As used herein, the term "acellular" refers to tissues with no live cells.

The term "decellular" refers to tissues in which cells are disintegrated and cellular material is extracted. The level of cell removal will depend on the exact source of tissue, the methodology used to extract the cell, and the need for the removal of cells. By cell removal a broad range of extraction may be used with the present invention. The amount of cell removal can range from very little to nearly 100 percent. The cell disintegration and/or extraction achieved renders the graft tolerated immunologically when using a non-autologous tissue source or a source of tissue that is not matched in terms of histocompatibility. Allografting requires less tissue extraction than xenografting to reduce concerns of immunologic rejection by the recipient. Therefore, longer contact times with amphoteric detergents are indicated.

The term "graft" as used herein refers to biological material derived from a donor for transplantation into a recipient. The graft can be derived from any animal source, including human, whether from cadavers or living donors. The donor is preferably a mammal.

The term "mammalian" refers to any animal recipient classified as a mammal, including humans, domestic and farm animals, and zoo, sports, or pet animals, such as dogs, horses, cats, pigs, and cows.

Method for Decellularization of Tissue Grafts

Tissue to be used in accordance with the subject invention can be harvested using standard techniques that are well-known to those skilled in the art. In a preferred embodiment, the tissue, which can be, for example, nerve tissue, is frozen after it is harvested.

In preferred embodiments, at least one detergent in a salt and buffered solution is used in the methods of the present invention. The detergent component preferably comprises at least one amphoteric detergent and excludes the use of any significant amount of ionic detergents (such as anionic detergents). In a preferred embodiment, the method does not use Triton X-200™.

Detergents used in the present invention are those that specifically rupture cells inside the tissue but do not disintegrate extracellular structures or structural proteins (those that include, for example, the extracellular matrix and/or laminin). Cellular debris may be removed as described herein by, for example, washing with buffered solutions and/or physically removing other non-structural debris such as fat. Compared to an untreated tissue graft, the replacement tissue of the subject invention elicits a significantly reduced immunologic response because surface cell antigens have been disintegrated or removed.

In a specific embodiment, a nerve tissue is obtained and subjected to a wash solution comprising at least one amphoteric detergent. The term "detergent" is used in this application interchangeably with the term "surfactant."

Amphoteric detergent can be broadly described as comprising molecules (or ions) that can react as an acid as well as a base. Amphoteric surfactants can include amphiprotic molecules that can either donate or accept a proton ($H^+$). These are greatly affected by changes in pH. They behave like anionic detergents at pH values greater or equal to 8. They behave like non-ionic detergents at pH values between 8 and 6. They behave like cationic detergents at a pH below 4. At a high pH, detergency powers are increased; at a low pH, detergency powers are reduced. In a preferred embodiment, tissue is contacted with a detergent that is amphoteric at pH 6 to 8. In a specific embodiment tissue contact with an amphoteric detergent is performed at a pH value between 4 and 8.

A listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic surfactants are a subset of amphoteric surfactants that includes ampholytes. Typically, a zwitterionic surfactant comprises a neutral molecule having a positive and negative electrical charge (n.b. not dipoles) at different locations within the molecule. Zwitterionics generally contain cationic and anionic groups that ionize to a nearly equal degree in the isoelectric region of the molecule and that can develop strong "inner-salt" attraction between positive-negative charge centers. Betaine and sultaine surfactants are exemplary zwitterionic surfactants for use herein. In one embodiment, the surfactant that is used is not a zwitterionic surfactant.

The concentrations of detergents (including the amphoteric sulfobetaines and anionic Triton X-200™) used in tissue decellularization schemes are based on their "critical micelle concentration." This concentration is reported in the literature or manufacturer's specification sheets and is a minimal requirement for detergent efficacy. The unique buffer rationale of the present invention, is that larger micelles extract better. Higher salt concentrations increase micelle size.

Thus, for example, large micelles form in the Extraction Buffer of the subject invention, which preferably has physiologic, or greater, salinity. These large micelles are advantageous for solubilizing cellular components. In preferred embodiments, the concentration of the detergent is at the critical micelle concentration, or higher.

Smaller micelles form in the Rinse Buffer, which has low (below physiological salinity), or no, tonicity/salinity/osmolarity. In accordance with the subject invention, it has been found that small micelles are better for diffusing out of the tissue and the low tonicity/salinity/osmolarity rinse (after a high salinity wash) creates an outward flow and aids extraction.

In preferred embodiments of the present invention, one or more initial tissue washes with a solution having a high concentration of NaCl maintains solubility and facilitates extraction by providing large micelles. Subsequent rinse(s) with a solution having a lower NaCl concentration decrease micelle size and improve diffusion out of the tissue.

In preferred embodiments, nerves are contacted with an Extraction Composition (preferably an aqueous composition) that comprises a detergent component that comprises, or consists of, one or more amphoteric detergents. Preferably, in the detergent component of the Extraction Composition there is an absence of anionic detergent. An "absence" of an anionic detergent, as that concept is set forth herein, means that there is not enough ionic detergent to degrade the ECM of the tissue. Thus, a complete absence (i.e. 0%) is not necessarily required. Preferably, the amount of anionic detergent is less than 0.14, 0.10, 0.05, 0.01, or 0.005%.

The amphoteric detergent can be, for example, SB-10 and/or SB-16. The concentration of the detergent(s) should be at least the critical micelle concentration. The concentration of SB-10 can be, for example, 100, 125, 150, 175, 200 or more mM. The concentration of SB-16 can be, for example, 0.5, 0.6, 0.7, 0.8, 0.9, 1.0, or more mM.

The Extraction Composition can further comprise, in addition to the detergent component, one or more salts and/or buffering systems. The salt concentration should be at, or above, physiological salinity. The lower end of the salt concentration may be, for example, 100, 125, 150, 175, 200 or more mM of NaCl and the upper limit may be, for example, 500, 450, 400, 350, 250 or less mM of NaCl. The pH can be, for example, from 6.5 to 8.5. Preferably the pH is at physiological pH. In one embodiment, a sodium phosphate buffer is used to maintain a pH of approximately 7.2.

The tissue can be contacted with this composition under gentle agitation for a period of time that is, preferably 5, 10, 15 or more hours.

Optionally, one or more additional extraction steps can be utilized with fresh Extraction Compositions, the ingredients of which can be the same as, or different from, the first Extraction Composition. This subsequent Extraction Composition, with the tissue contained therein, can then be agitated for 1, 2, 3, 4, 5, 6 or more hours.

The extraction steps are preferably followed by washes with Extraction Buffer and/or physiological saline, preferably, followed by a wash with a Rinse Buffer. The Rinse Buffer can have the same or different buffer system as the Extraction Buffer and would also be typically at the same or similar pH. The salt concentration of the Rinse Composition is, however, preferably, less than the salinity of the Extraction Composition. In one embodiment, the Rinse Composition has no salinity.

The steps of the process will typically be performed at 20° to 30° C. and, preferably, at or near room temperature (e.g. 25° C.).

In a preferred embodiment, the method comprises a final wash with a large volume of Rinse Buffer and the tissue can be resuspended in Rinse Buffer, then placed in physiologic buffered saline and, preferably, frozen until used.

The buffer system and amphoteric detergents used in the present invention achieve equivalent, or better, decellularization to that of Hudson et al., which uses harsh anionic detergent extraction. Human nerves processed by the method of Hudson et al., showed substantially more cellular residuals than reported for rat nerves. In addition, the methods used by Hudson et al. and the present invention achieve nearly identical levels of cellular extraction when applied to rabbit and human nerves. Therefore, the addition of the anionic detergent Triton X-200™ as described by Hudson et al. has no apparent advantage in decellularization and, as described above, is detrimental to the growth-promoting properties of the nerve sheath structures. Furthermore, Hudson et al. use "fresh" nerves compared to the present invention which, preferably, uses nerves frozen immediately after acquisition, which also allows for more efficient use of nerves from human cadaveric donors.

Advantageously, the decellularization method of the subject invention yields tissue grafts with excellent physiological and structural properties for facilitating and promoting tissue regeneration. For example, a high percentage of extracellular matrix is preserved. In preferred embodiments, this percentage is greater than 50, 60, 70, 75, 80, 85, 90, 95, or 99%.

In the specific case of nerve grafts, after the decellularization process, greater than 50, 60, 70, 75, 80, 85, 90, 95 or 99% of laminin is retained. This can be measured by, for example, observational (double-blinded) scoring or digital image analysis compared to unprocessed control donor nerve.

The advantageous properties of the nerve grafts produced according to the subject invention can also be measured in terms of their neurite-promoting activity as measured by a bioassay. One such bioassay is the cryoculture assay. In preferred embodiments, nerve grafts produced according to the decellularization techniques of the subject invention retain 50, 60, 70, 75, 80, 85, 90, 95, or 99% of their neurite promoting activity, compared to control nerves that are, for example, treated with buffer washes only.

In one embodiment, tissues including nerve, muscle, placental, and vascular are decellularized according to the subject invention and used as grafts to repair nerves. In a preferred embodiment, decellularized nerves according to the present invention are used as orthotopic grafts to repair nerves.

In one embodiment, decellularized nerves according to the present invention are used in veterinary allogeneic applications, including, but not limited to, horse nerve grafts into horses, cat nerve grafts into cats, and dog nerve grafts into dogs.

In another embodiment, decellularized nerves according to the present invention are used in xenograft applications, including animal donor nerves grafted into human recipients and animal donor nerves grafted into animal recipients of a different species.

The present decellularization method can also be used for tissue grafts other than for nerve repair, including, but not limited to, bone grafts, intestinal grafts, vascular grafts, ligament grafts, tendon grafts, and heart valve grafts.

In a preferred embodiment of the subject invention grafts are frozen after decellularization. This facilitates a favorable state for gamma irradiation (the most common means of sterilization). In addition, shipping and storage of the frozen final graft product is more practical.

Cellular Repopulation of Grafts

While cells are disintegrated and extracted from the tissue of the present invention, it may be acceptable and often necessary to reintroduce one or more different types of cells to the replacement tissue. These cells may be obtained directly from a donor, from a culture of cells from a donor, or from cell culture. Donor cells are generally obtained by biopsy and grown to confluence in culture using standard conditions. The recipient may be immunosuppressed as needed, for example, using a schedule of steroids and/or other immunosuppressant drugs, if required. Immunosuppression of the recipient may provide immunoprotection of replacement tissue transplants while a new tissue or tissue equivalent is growing.

In addition, a replacement tissue of the present invention may be used to provide multiple cell types, including genetically altered cells, clones or transplants, within the three-dimensional architecture/structure of the replacement tissue for the purpose of transplant engraftment, immunotherapy, cognitive function, tissue regeneration, repair or reconstruction. Examples of such cells include, but are not limited to, chondrocyte, osteoblast, muscle cell, thyroid cell, parathyroid cell, immune cell, pancreatic cell, fibroblast, hepatocyte, epithelial cell, islet cell, nerve cell, and other cells acting primarily to synthesize and secrete or metabolize materials, as well as biopsied or cloned cells of the intestines, kidney, heart, brain, spinal cord, muscle, skeleton, liver, stomach, skin, lung, reproductive system, nervous system, immune system, spleen, bone marrow, lymph nodes, glands.

Grafts as Carriers for Bioactive Molecules

A replacement tissue of the present invention may also include bioactive molecules formulated with one or more active species so that the replacement tissue becomes a carrier for one or more active species. A kit or replacement tissue of the invention may include active agents incorporated into an added polymer or polymer solution (e.g., a polymer scaffold) or may be attached directly to the surface of or within the replacement tissue using techniques readily apparent to those skilled in the art. For example, the active agents may be added by curing on and into the cell-free replacement tissue, bonded ionically, covalently and/or using a crosslinking agent, e.g., a cleavable cross-linking agent.

The active agent may be a drug or other biologically active compound; thus a replacement tissue of the present invention may be a microcarrier for the delivery of drugs or other biologically active compounds when used in the body. Examples of biologically active compounds are proteins, peptides, polysaccharides, nucleic acids, oligonucleotides, natural and synthetic organic or inorganic molecules, and those biologic molecules used for therapeutic, prophylactic or diagnostic purposes. Drugs may include antibiotics, antivirals, chemotherapeutic agents, immunosuppressive agents, growth factors, anti-angiogenic agents, hormones, anti-inflammatory agents, drugs having an effect on vascular flow, cellular metabolics, or that are effective against one or more diseases and/or combinations thereof.

Other active agents may also be included with a replacement tissue or kit of the present invention, e.g., non-steroidal anti-inflammatory drugs (NSAIDs) such as propionic acid derivatives; acetic acid derivatives; fenamic acid derivatives; biphenylcarboxylic acid derivatives; and oxicams. Analgesics for use with a kit or replacement tissue of the present invention include acetominophen and phenacetin.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Decellularization Process

All procedures should employ aseptic techniques and sterile solutions. Following are the steps of one embodiment of the decellularization process of the subject inventon.
1. Resect nerve from a donor and store frozen.
2. Thaw the nerve at room temperature. Rinse with chilled water. Submerge in a large volume of chilled water. Gently agitate at 4° C. for 6 hrs (or longer).
3. Submerge the nerves in a large volume of 125 mM (or more concentrated) Sulfobetaine-10 in Extraction Buffer (10 mM Na phosphate buffer, pH 7.2+150 mM NaCl) or any physiologic saline. Gently agitate at 25° C. (near room temperature) for 15 hrs (or longer).
4. Replace with a large volume of fresh 125 mM (or more concentrated) Sulfobetaine-10 in Extraction Buffer or any physiologic saline. Agitate for 6 hrs (or longer) at 25° C.
5. Wash with a large volume of Extraction Buffer or any physiologic saline. Agitate at 25° C. for 60 min (or longer).
6. Wash with a large volume of Rinse Buffer (10 mM Na phosphate buffer, pH 7.2) or any buffer with very low tonicity (no salinity). Agitate for 60 min (or longer) at 25° C.
7. Submerge the nerves in a large volume of 0.6 mM (or more concentrated) Sulfobetaine-16 in Extraction Buffer or any physiologic saline. Agitate for 15 hrs (or longer) at 25° C.
8. Replace with a large volume of fresh 0.6 mM (or more concentrated) Sulfobetaine-16 in Extraction Buffer or any physiologic saline. Agitate for 6 hrs (or longer) at 25° C.
9. Wash with a large volume of Extraction Buffer or any physiologic saline. Gently agitate the nerves for 30 minutes (or longer) and then replace with fresh Extraction Buffer or any physiologic saline. Wash for 15 hrs with agitation at 4° C.
10. Wash with a large volume of Rinse Buffer. Gently agitate to resuspend the nerves and then replace with fresh Rinse Buffer or any buffer with very low tonicity (no salinity). Wash for 3 hrs with agitation at 4° C.
11. Place in physiologic buffered saline and store frozen.

Example 2

Comparison of Decellularization Method with Rabbit Nerves

Grafts prepared in accordance with the subject invention as described above are referred to as DC3 grafts. DC3 grafts were compared to normal (unprocessed) rabbit nerve and rabbit grafts processed by the protocol described by Hudson et al., (Tissue Engineering 10:1346-1358, 2004) and U.S. Pat. No. 7,402,319; referred to herein as DC2 grafts.

The DC2 and DC3 grafts from the two processing methods were evaluated by several histological techniques. Results of each evaluation were semi-quantitatively scored (0=Not extracted, 1=Partially extracted, 2=Mostly extracted, 3=Fully extracted and R=Redistributed). Results for the two detergent processing schemes (DC2, DC3) and normal nerve control are shown in FIGS. 1-6.

FIG. 1 illustrates hematoxylin and eosin (H&E) stains of rabbit nerve tissue (control; panel A), rabbit nerve tissue processed in accordance with the process taught by Hudson et al. (DC2; panel B), and rabbit nerve tissue processed in accordance with the method taught by the subject invention (DC3; panel C). Panel A had a score of zero. Panels B (DC2) and C (DC3) each had a score of 2. H&E staining is a staining method for general histology. These panels and scores demonstrate that the processing methods for DC2 and DC3 achieved extensive cellular extraction and retention of overall nerve sheath integrity.

Figure 2:
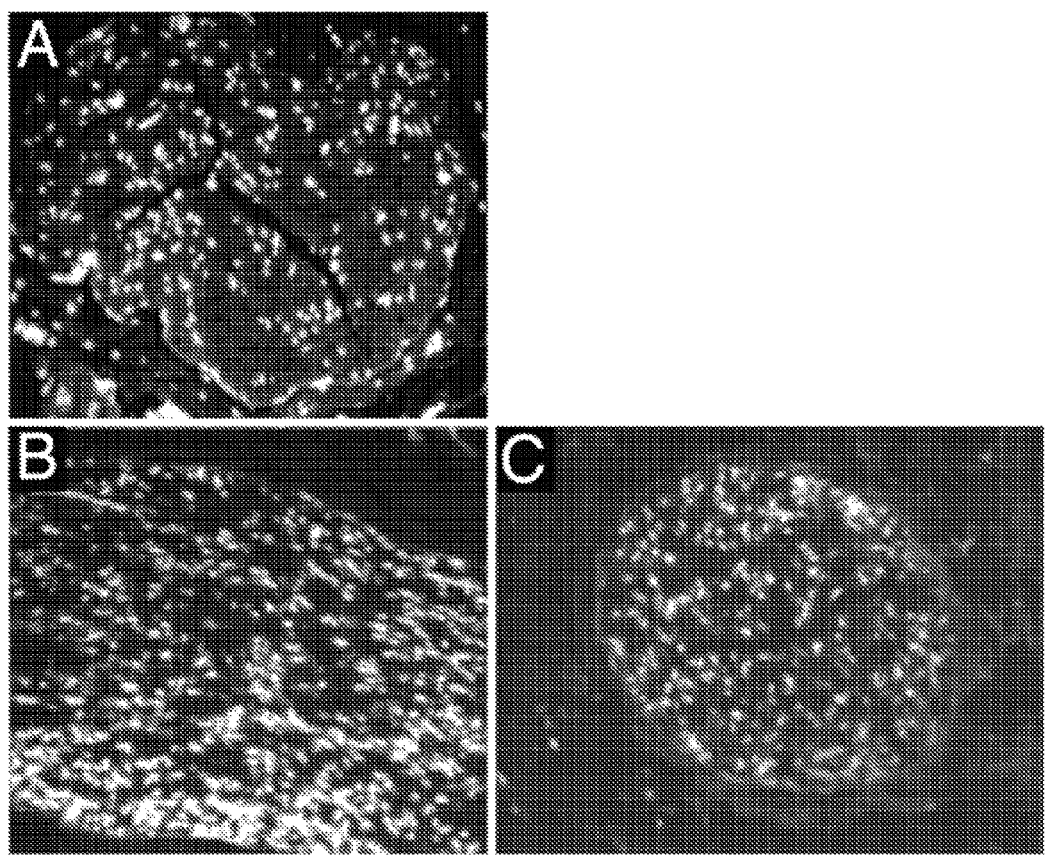
FIG. 2. Hoescht staining of rabbit nerve tissue (control; panel A), rabbit nerve tissue processed in accordance with the process taught by Hudson et al. (DC2; panel B), and rabbit nerve tissue processed in accordance with the method of the subject invention (DC3; panel C).

FIG. 2 illustrates Hoescht staining of rabbit nerve tissue (control; panel A), rabbit nerve tissue processed in accordance with the process taught by Hudson et al. (DC2; panel B), and rabbit nerve tissue processed in accordance with the method taught by the subject invention (DC3; panel C). Panel A had a score of zero. Panels B (DC2) and C (DC3) each had a score of 1 R. Hoescht staining is a staining method for DNA. These panels and scores show the processing methods for DC2 and DC3 did not eliminate DNA but rather dispersed and redistributed DNA.

Figure 3:
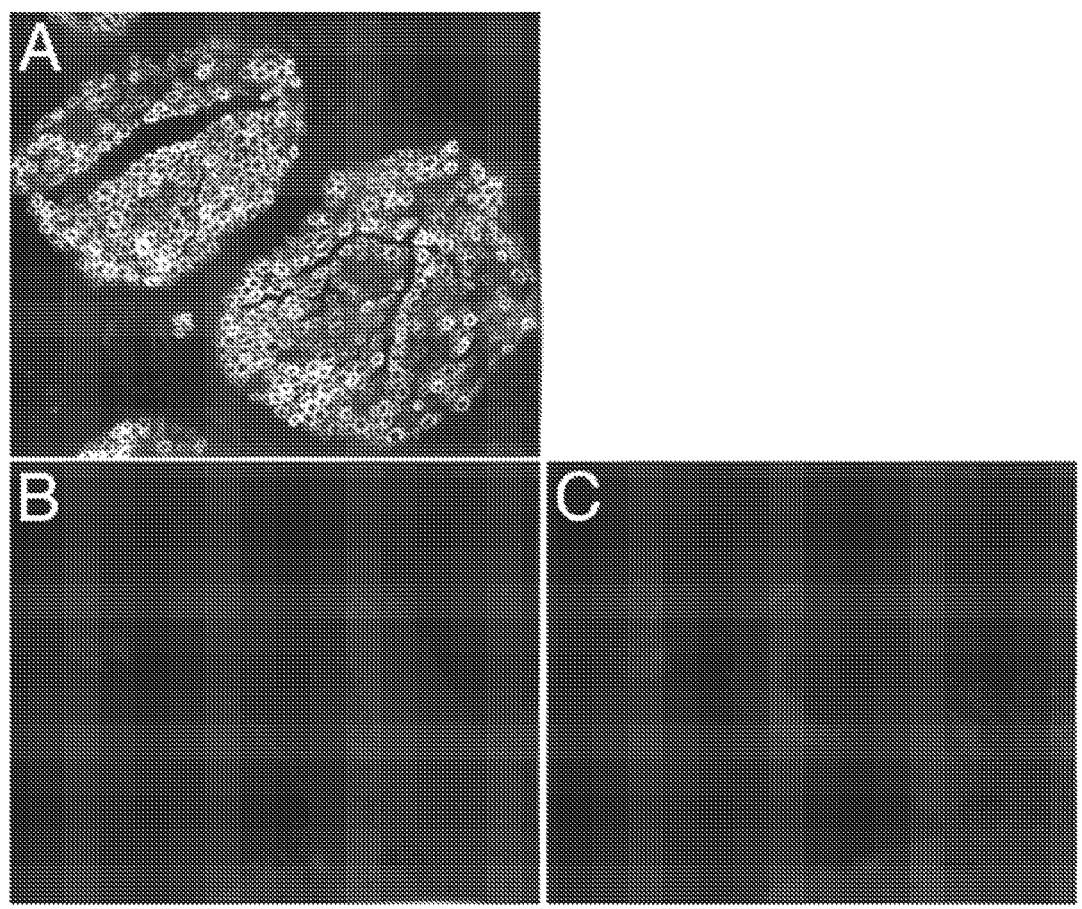
FIG. 3. S-100 Immunostaining of rabbit nerve tissue (control; panel A), rabbit nerve tissue processed in accordance with the process taught by Hudson et al. (DC2; panel B), and rabbit nerve tissue processed in accordance with the method of the subject invention (DC3; panel C).

FIG. 3 illustrates S-100 Immunostaining of rabbit nerve tissue (control; panel A), rabbit nerve tissue processed in accordance with the process taught by Hudson et al. (DC2; panel B), and rabbit nerve tissue processed in accordance with the method taught by the subject invention (DC3; panel C). Panel A had a score of zero. Panels B (DC2) and C (DC3) each had a score of 3. S-100 Immunolabeling (a cytoplasmic protein in Schwann cells) showed the DC2 and DC3 processing methods to be equally effective in extracting the cytoplasm of Schwann cells.

Figure 4:
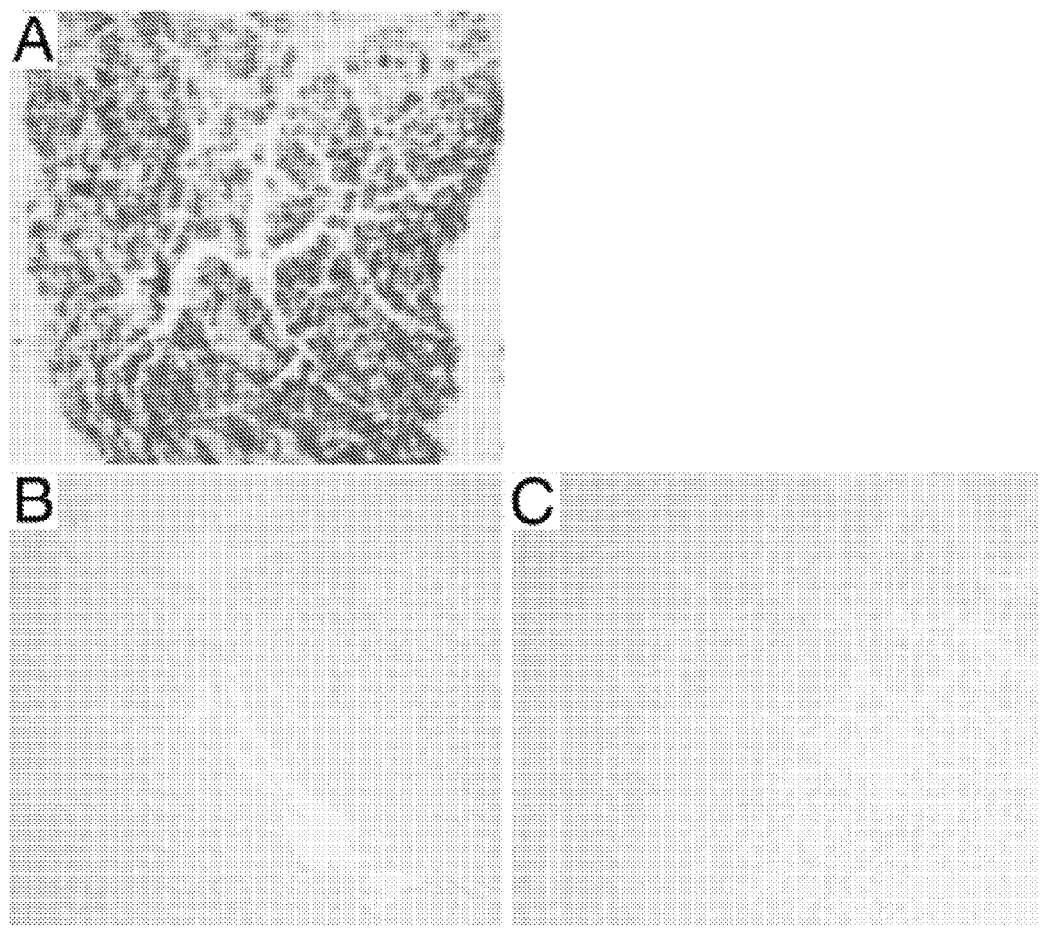
FIG. 4. Sudan Black staining of rabbit nerve tissue (control; panel A), rabbit nerve tissue processed in accordance with the process taught by Hudson et al. (DC2; panel B), and rabbit nerve tissue processed in accordance with the method of the subject invention (DC3; panel C).

FIG. 4 illustrates Sudan Black staining of rabbit nerve tissue (control; panel A), rabbit nerve tissue processed in accordance with the process taught by Hudson et al. (DC2; panel B), and rabbit nerve tissue processed in accordance with the method taught by the subject invention (DC3; panel C). Panel A had a score of zero. Panels B (DC2) and C (DC3) each had a score of 3. Sudan Black staining is a staining method for myelin. These panels and scores demonstrate that the processing methods for DC2 and DC3 were equally and highly effective at extracting myelin.

Figure 5:
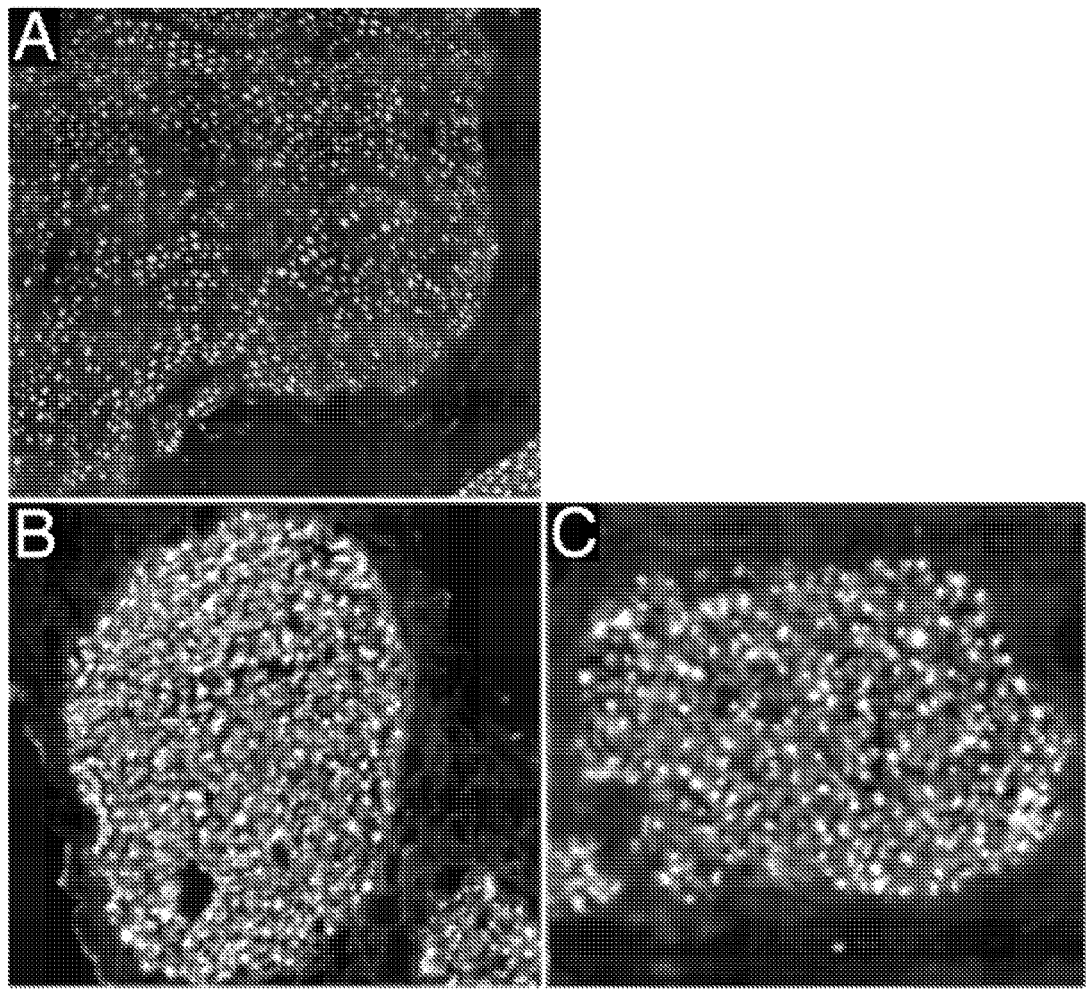
FIG. 5. NAP-4 Neurofilament staining of rabbit nerve tissue (control; panel A), rabbit nerve tissue processed in accordance with the process taught by Hudson et al. (DC2; panel B), and rabbit nerve tissue processed in accordance with the method of the subject invention (DC3; panel C).

FIG. 5 illustrates NAP-4 Neurofilament immunostaining of rabbit nerve tissue (control; panel A), rabbit nerve tissue processed in accordance with the process taught by Hudson et al. (DC2; panel B), and rabbit nerve tissue processed in accordance with the method taught by the subject invention (DC3; panel C). Panel A had a score of zero. Panels B (DC2) and C (DC3) each had a score of 1 R. Neurofilament Immunolabeling (a marker of the neuronal/axonal cytoskeleton) showed the processing methods for DC2 and DC3 only partially extracted and redistributed the axonal cytoskeleton.

Figure 6:
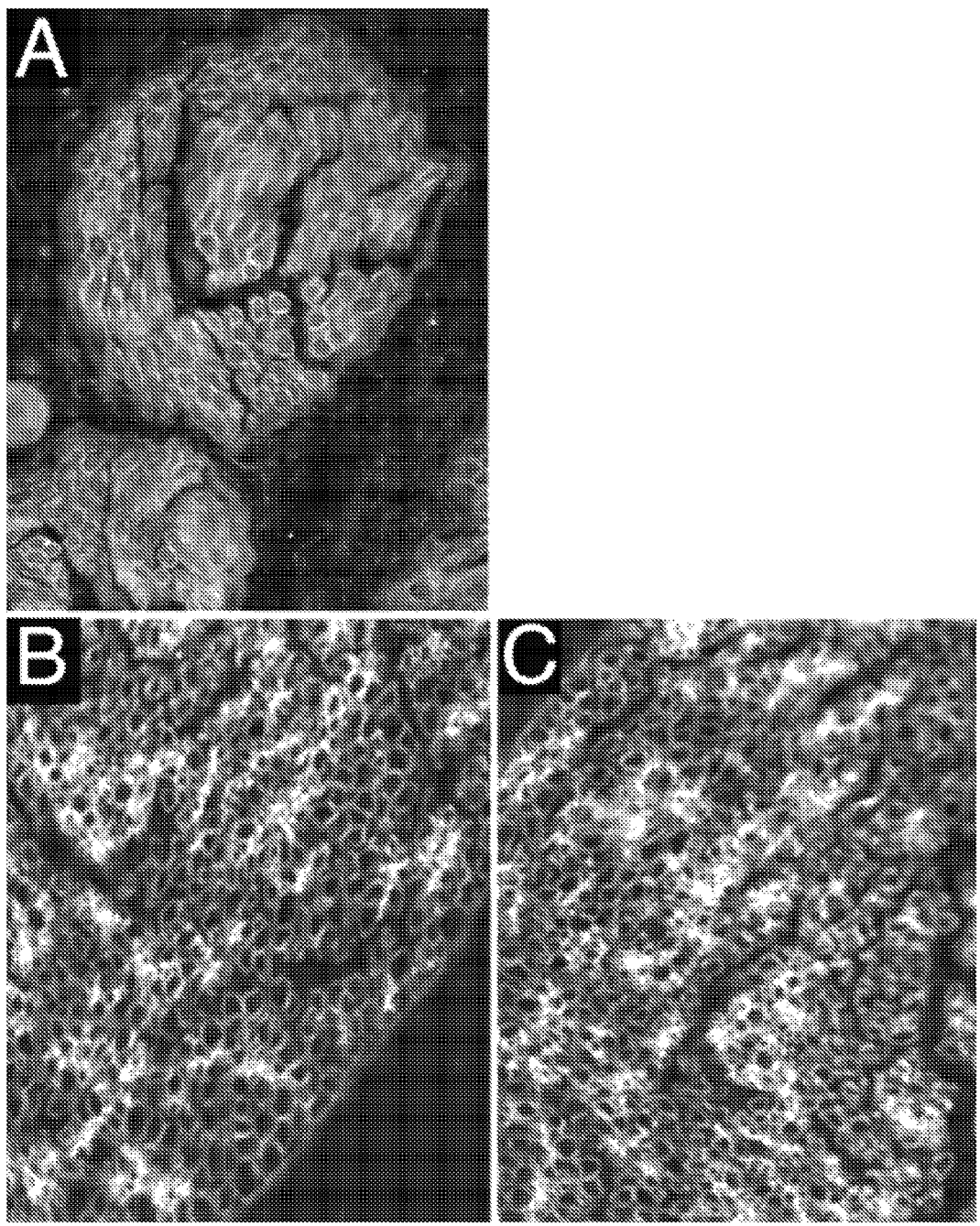
FIG. 6. Laminin immunostaining of rabbit nerve tissue (control; panel A), rabbit nerve tissue processed in accordance with the process taught by Hudson et al. (DC2; panel B), and rabbit nerve tissue processed in accordance with the method of the subject invention (DC3; panel C).

FIG. 6 illustrates laminin immunostaining of rabbit nerve tissue (control; panel A), rabbit nerve tissue processed in accordance with the process taught by Hudson et al. (DC2; panel B), and rabbit nerve tissue processed in accordance with the method taught by the subject invention (DC3; panel C). Panel A had a score of zero. Panels B (DC2) and C (DC3)

each had a score of 1 R. Laminin is a major component of nerve sheaths including the important basal lamina surrounding axons. Laminin immunolabeling showed the processing methods of DC3 did not substantially extract the basal lamina structure.

Example 3

Immunocompatibility of Nerve Grafts

Extensive in vivo testing in New Zealand White (NZW) rabbits has been performed with nerve grafts processed by the Hudson et al. method and the subject invention. Results show that both types of decellularized nerve grafts were immunologically compatible and no graft rejection was observed.

NZW rabbits are an outbred strain. It is known in the literature that allografting of live or cellular tissues from a NZW rabbit donor to NZW recipient results in graft immunorejection.

Therefore, the observed lack of graft rejection in NZW allografts demonstrates that nerve allografts prepared by the subject invention are immunocompatible.

Example 4

Comparison of Decellularization Method with Human Nerves

Human nerve tissue was prepared in accordance with the subject invention as described above and referred to as DC3 grafts. DC3 grafts were compared to normal (unprocessed) human nerve and human grafts processed by the protocol described by Hudson et al., (Tissue Engineering 10:1346-1358, 2004) and U.S. Pat. No. 7,402,319; referred to herein as DC2 grafts. The DC2 and DC3 grafts from the two processing methods were evaluated by several histological techniques.

Figure 7:
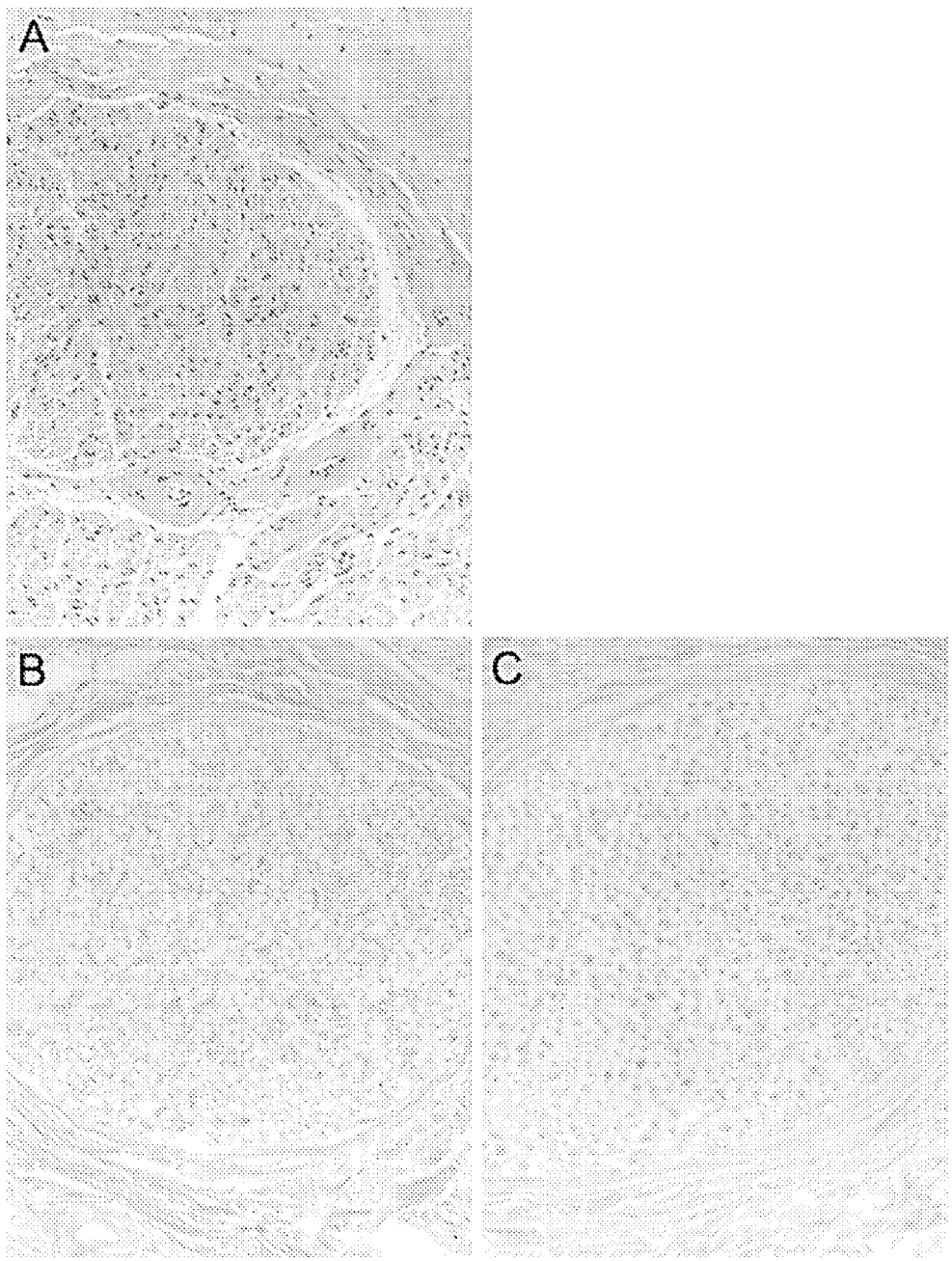
FIG. 7. Hematoxylin and eosin staining of human nerve tissue (control; panel A), human nerve tissue processed in accordance with the process taught by Hudson et al. (DC2; panel B), and human nerve tissue processed in accordance with the method of the subject invention (DC3; panel C).

FIG. 7 illustrates a Hematoxylin and eosin staining of human nerve tissue (control; panel A), human nerve tissue processed in accordance with the process taught by Hudson et al. (DC2; panel B), and human nerve tissue processed in accordance with the method taught by the subject invention (DC3; panel C).

Figure 8:
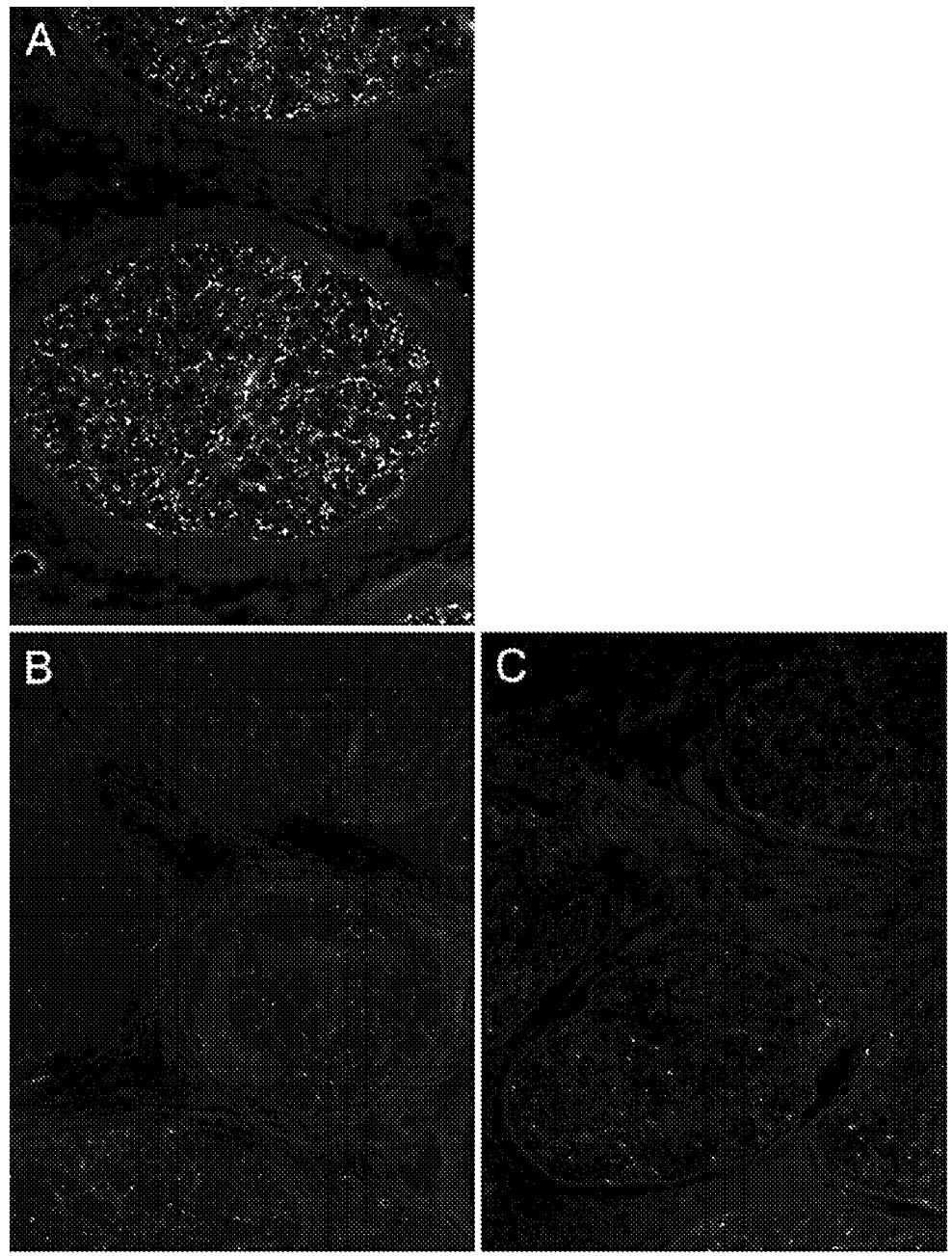
FIG. 8. Hoescht staining of human nerve tissue (control; panel A), human nerve tissue processed in accordance with the process taught by Hudson et al. (DC2; panel B), and human nerve tissue processed in accordance with the method of the subject invention (DC3; panel C).

FIG. 8 illustrates a Hoechst staining of human nerve tissue (control; panel A), human nerve tissue processed in accordance with the process taught by Hudson et al. (DC2; panel B), and human nerve tissue processed in accordance with the method taught by the subject invention (DC3; panel C).

Figure 9:
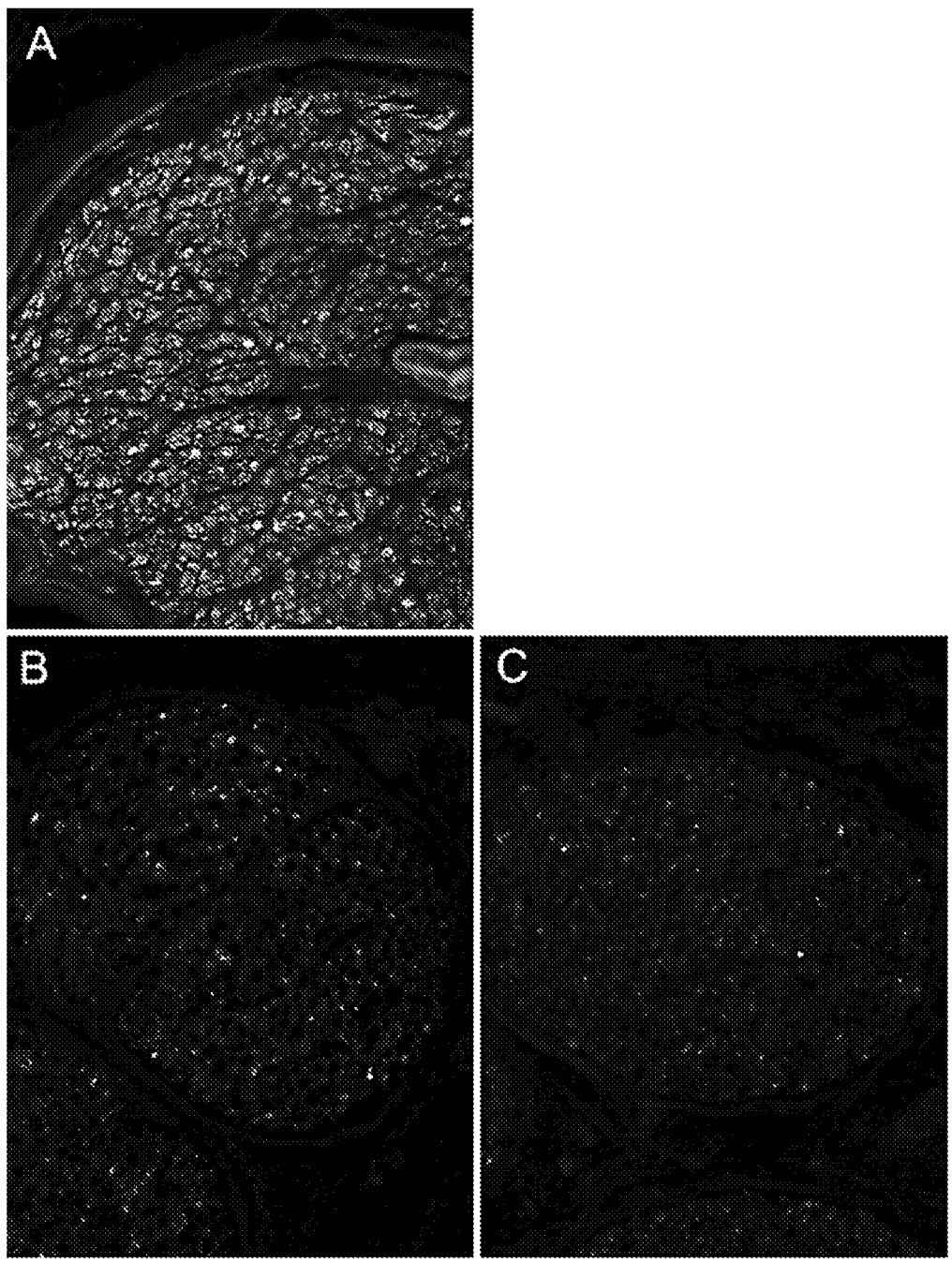
FIG. 9. S-100 immunostaining of human nerve tissue (control; panel A), human nerve tissue processed in accordance with the process taught by Hudson et al. (DC2; panel B), and human nerve tissue processed in accordance with the method of the subject invention (DC3; panel C).

FIG. 9 illustrates a S-100 immunostaining of human nerve tissue (control; panel A), human nerve tissue processed in accordance with the process taught by Hudson et al. (DC2; panel B), and human nerve tissue processed in accordance with the method taught by the subject invention (DC3; panel C).

Figure 10:
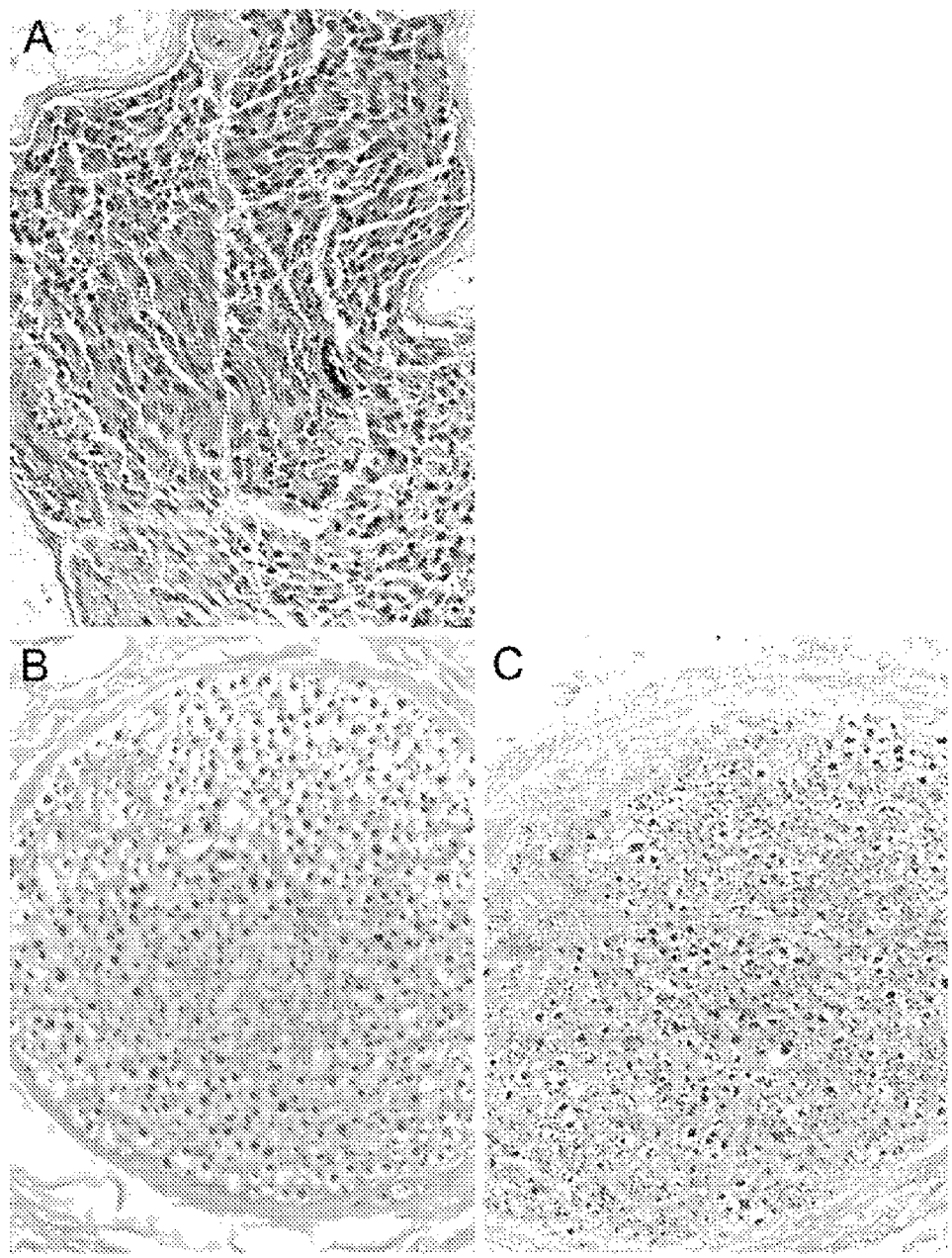
FIG. 10. Sudan Black staining of human nerve tissue (control; panel A), human nerve tissue processed in accordance with the process taught by Hudson et al. (DC2; panel B), and human nerve tissue processed in accordance with the method of the subject invention (DC3; panel C).

FIG. 10 illustrates a Sudan Black staining of human nerve tissue (control; panel A), human nerve tissue processed in accordance with the process taught by Hudson et al. (DC2; panel B), and human nerve tissue processed in accordance with the method taught by the subject invention (DC3; panel C).

Figure 11:
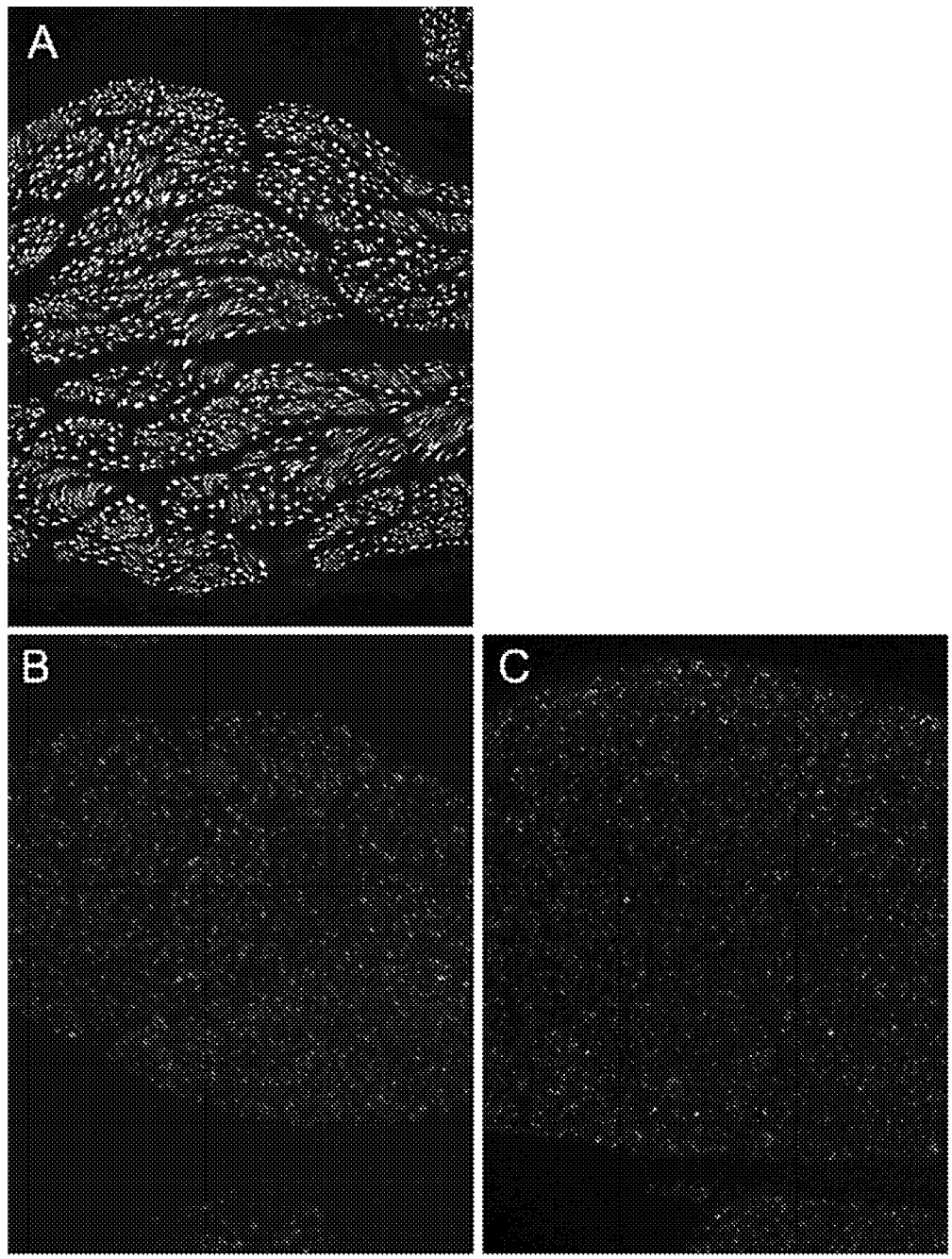
FIG. 11. NAP-4 Neurofilament immunostaining of human nerve tissue (control; panel A), human nerve tissue processed in accordance with the process taught by Hudson et al. (DC2; panel B), and human nerve tissue processed in accordance with the method of the subject invention (DC3; panel C).

FIG. 11 illustrates a NAP-4 Neurofilament immunostaining of human nerve tissue (control; panel A), human nerve tissue processed in accordance with the process taught by Hudson et al. (DC2; panel B), and human nerve tissue processed in accordance with the method taught by the subject invention (DC3; panel C).

Figure 12:
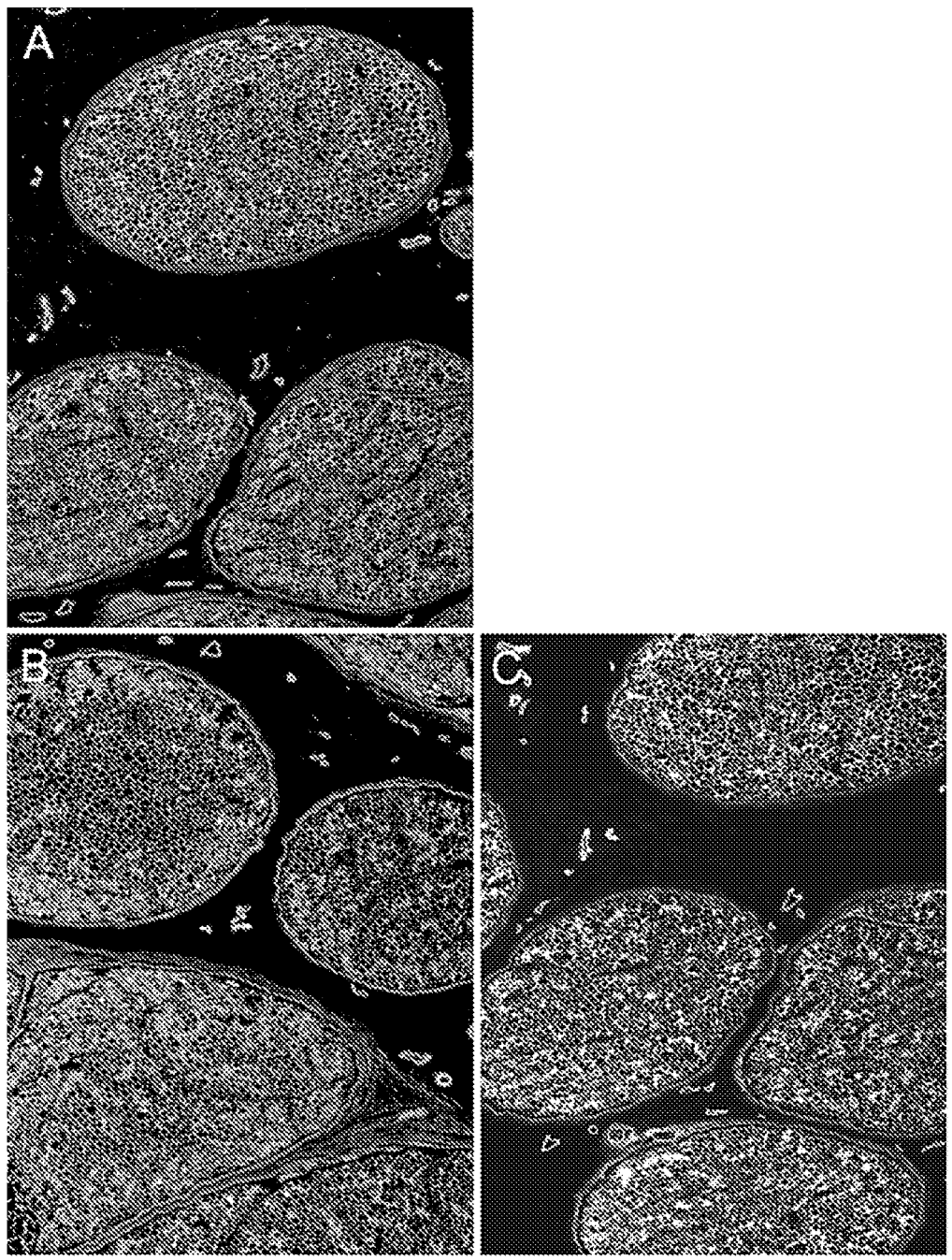
FIG. 12. Laminin immunostaining of human nerve tissue (control; panel A), human nerve tissue processed in accordance with the process taught by Hudson et al. (DC2; panel B), and human nerve tissue processed in accordance with the method of the subject invention (DC3; panel C).

FIG. 12 illustrates a Laminin immunostaining of human nerve tissue (control; panel A), human nerve tissue processed in accordance with the process taught by Hudson et al. (DC2; panel B), and human nerve tissue processed in accordance with the method taught by the subject invention (DC3; panel C).

Example 5

Neuron Repopulation of Rat Nerve Grafts

Nerves were cryosectioned on the longitudinal axis and mounted on coverslips. Dissociated neurons were seeded onto the tissue sections and cultured for 24 hr. The cryocultures were then fixed and test neurons were immunostained.

Figure 13A:
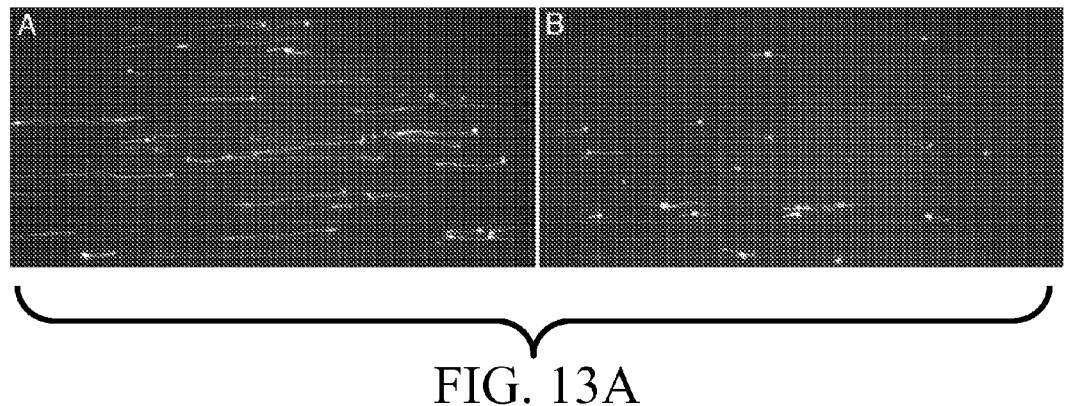
FIG. 13A. Cryoculture assay of rat nerve grafts decellularized by (A) buffer alone and (B) detergent decellularization described by Hudson et al. (sulfobetaine-10, sulfobetaine-16 and Triton X-200™). Nerves were cryosectioned on the longitudinal axis and mounted on coverslips. Dissociated neurons were seeded onto the tissue sections and cultured for 24 hr. The cryocultures were then fixed and test neurons were immunostained. Extensive axonal growth was observed in the buffer alone condition while the growth-promoting activity of the nerve grafts was virtually eliminated by the rigorous detergent decellularization.

FIG. 13A illustrates a cryoculture assay of rat nerve grafts decellularized by (A) buffer alone and (B) detergent decellularization described by Hudson et al. (sulfobetaine-10, sulfobetaine-16 and Triton X-200™). Extensive axonal growth was observed in the buffer alone condition while the growth-promoting activity of the nerve grafts was virtually eliminated by the rigorous detergent decellularization.

Figure 13B:
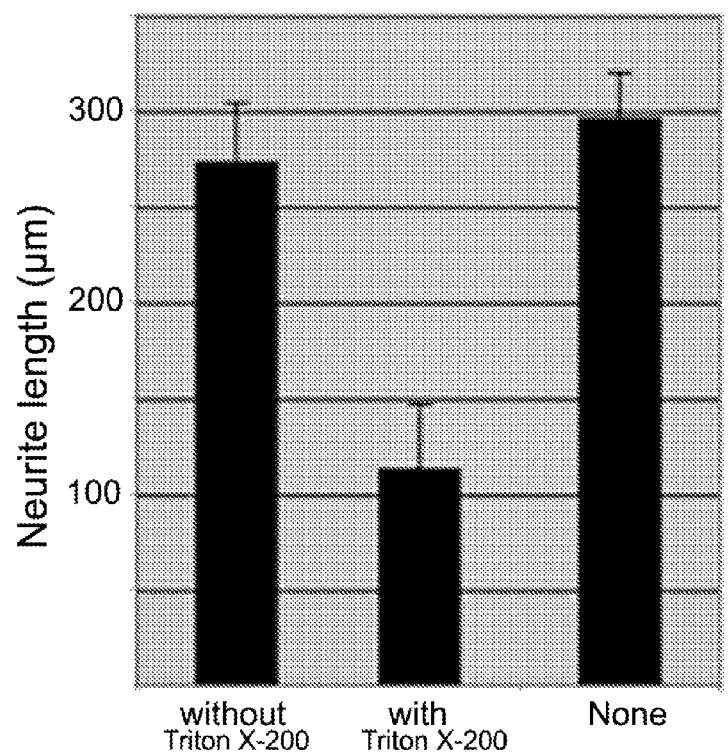
FIG. 13B. Effects of Triton X-200™ on the neurite-promoting activity of nerve grafts. Nerve graft samples were decellularized by the method of Hudson et al. with and without Triton X-200™. Nerves were cryosectioned on the longitudinal axis and mounted on coverslips. Dissociated neurons were seeded onto the tissue sections and cultured for 24 hr. Neurite lengths were scored by digital image analysis. Data represent the mean (±SE) scores of more than 500 axons from 4 tissue sections in 2 separate experiments.

Cryoculture assays were performed on nerves decellularized by the method of Hudson et al. with and without Triton X-200™ (FIG. 13B). Control nerves (treated with buffer washes only) had high neurite-promoting activity. Decellularization of nerves with sulfobetaine-10 and sulfobetaine-16 (without Triton X-200™) had similarly high neurite-promoting activity. In contrast, decellularization with the addition of Triton X-200™ reduced neurite-promoting activity significantly. These results show that Triton X-200™ has a persistent deleterious effect on the biological properties of decellularized nerve grafts.

Example 6

Effects of Detergents on Neurite-Promoting Activity of Laminin

Figure 14:
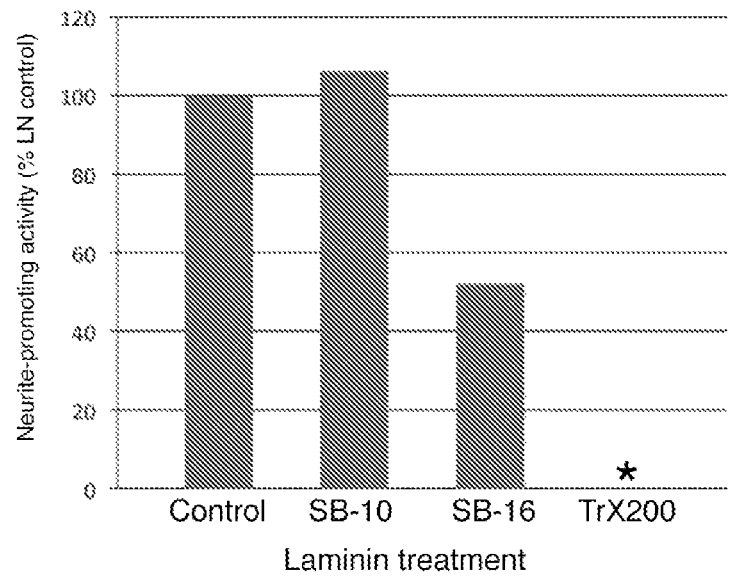
FIG. 14. Effects of individual detergents on the neurite-promoting activity of purified laminin. Purified laminin-1 was mixed with individual detergents as follows: Control (buffer alone), sulfobetaine-10 (125 mM), sulfobetaine-16 (0.6 mM) and Triton X-200 (0.14%). The mixtures were extensively dialyzed and then were added to tissue culture wells to form a substratum onto which dissociated neurons were seeded. After 24 hours in culture the length of neurites were measured. Data represent the specific activities (ED50) calculated from mean scores from dilution series performed in duplicates in 4 separate experiments FIG. 15. Successful nerve regeneration in a rabbit nerve allograft model. A 0.5 cm gap in the rabbit peroneal nerve was repaired with a 1.2 cm nerve graft processed by the method of the subject invention. After 4 weeks the grafts were examined. A) Hematoxylin and eosin staining indicated excellent graft integrity and incorporation into the recipient nerve. Revascularization and cellular infiltration are evident within the graft. No signs of inflammation or graft rejection were found in any of the 24 recipients. B) β-tubulin III immunolabeling (specific for axons) revealed abundant axonal regeneration throughout the graft. C) S100 immunolabeling revealed abundant recipient tissue Schwann cells had infiltrated the graft in close association with regrowing axons, indicative of functional nerve regeneration.
Figure 15:
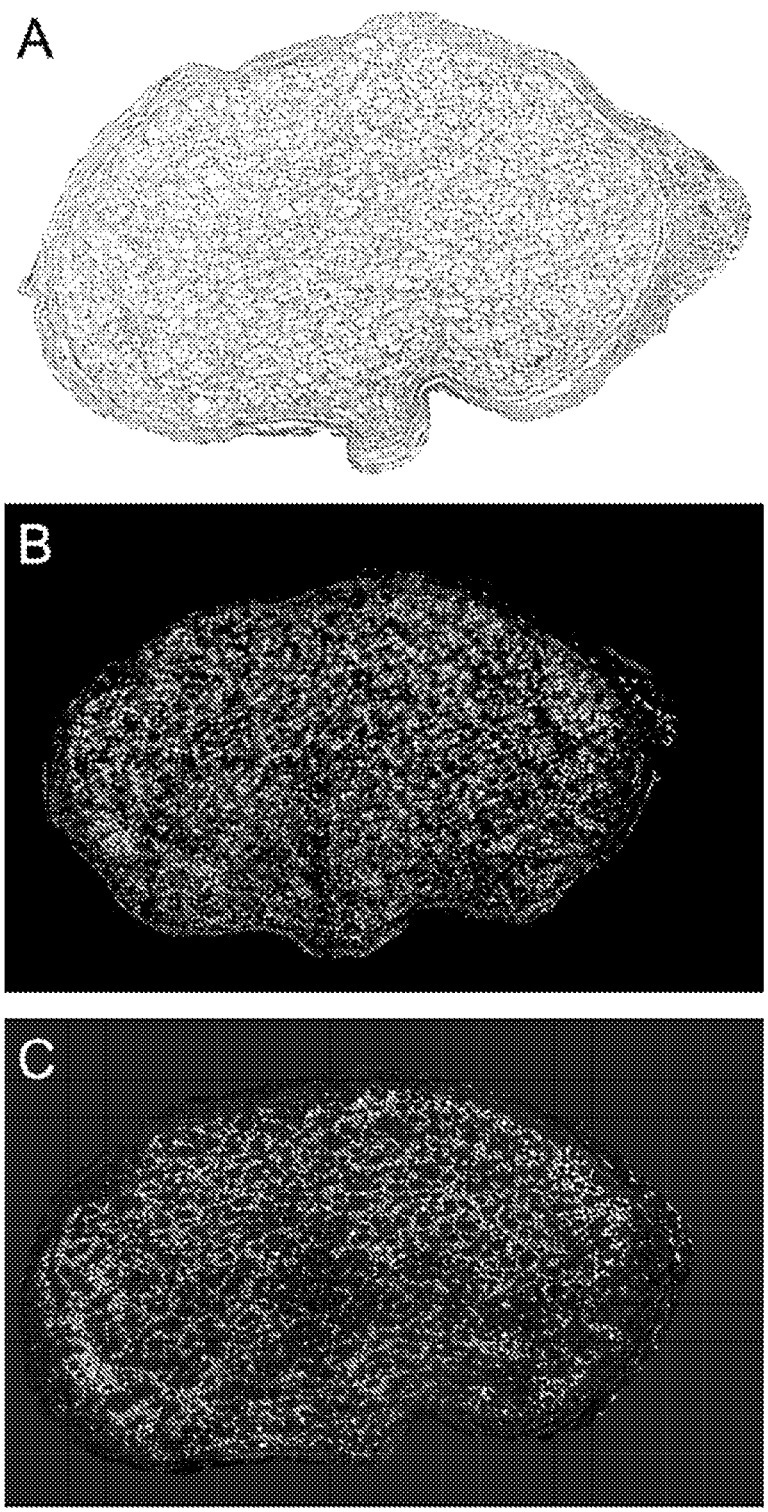
Figure 16:
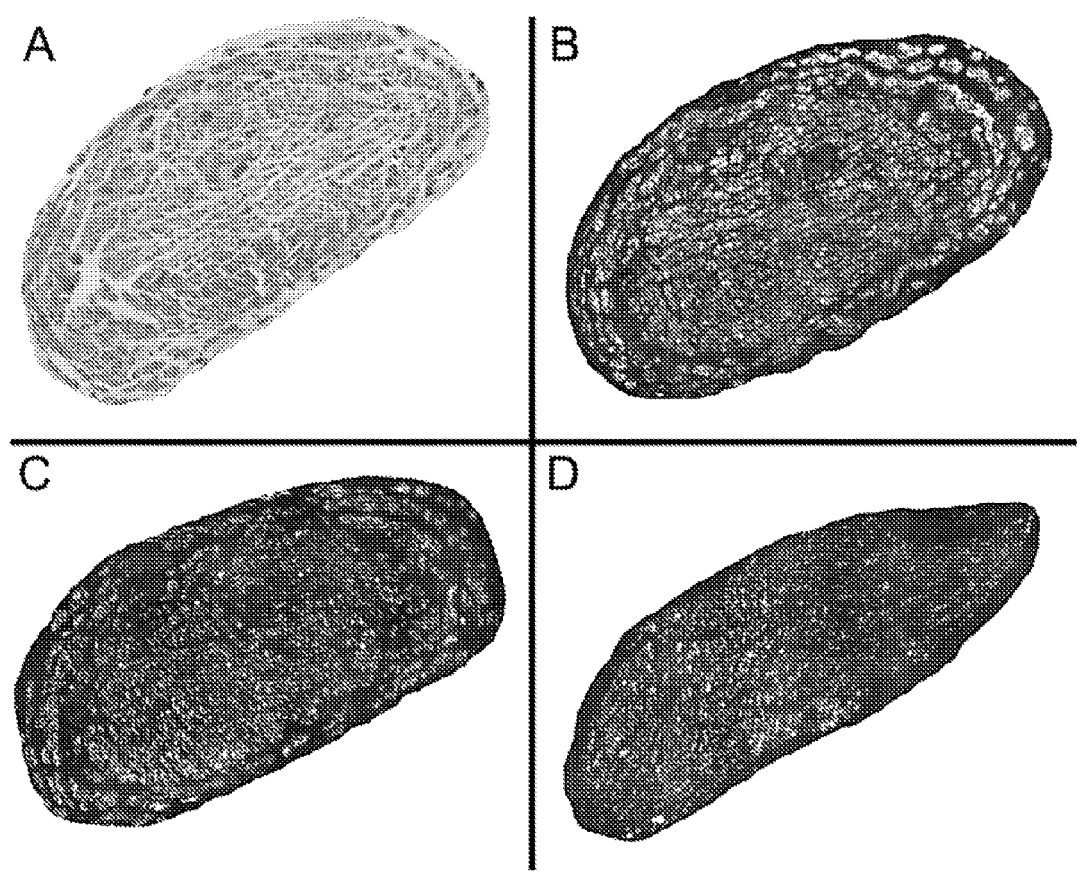
FIG. 16. Successful regeneration through very long nerve allografts. A 5 cm gap in the rabbit peroneal nerve was repaired with a 7 cm nerve graft processed by the method of the subject invention. After 26 weeks the grafts were examined. A) Hematoxylin and eosin staining indicated excellent graft integrity and incorporation into the recipient nerve. Revascularization and cellular infiltration are evident within the graft. No signs of inflammation or graft rejection were found in any of the 10 recipients. B) NAP-4 neurofilament immunolabeling (specific for axons) revealed abundant axonal regeneration throughout the graft. C) S100 immunolabeling revealed abundant recipient tissue Schwann cells had infiltrated the graft in close association with regrowing axons, indicative of functional nerve regeneration. D) Abundant neurofilament immunopositive axons were found in the recipient nerve distal to the graft, indicating that nerve regeneration successfully traversed the 7 cm graft and proceeded distally to target tissues.

The extracellular matrix of nerve is known to promote the growth of axons. In particular, the basal lamina tubes encasing axons provides a potent stimulus for axonal growth in nerve regeneration. The cryoculture assay used in the experiments described above relies on the structure and growth-promoting activity of the basal lamina. It is well documented that laminin is the major neurite-promoting component of the nerve basal lamina. This is readily demonstrated in the cryoculture assay wherein neurite growth is effectively inhibited by pretreatment of nerve tissue sections with function blocking anti-laminin antibody. Therefore, tests were performed to examine the effects of individual detergents on purified laminin. Laminin activity was unchanged by SB-10. Exposure to SB-16 reduced laminin activity approximately 50%. TrX200 (an anionic detergent) essentially eliminated laminin's neurite-promoting activity (FIG. 14).

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention, i.e., compositions and methods for decellularization of tissue grafts. For instance, by using "consisting essentially of," the compositions do not contain any unspecified ingredients including, but not limited to, surfactants that have a direct beneficial or adverse effect on decellularization of tissue.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The invention claimed is:

1. A method for decellularizing a tissue graft wherein said method comprises contacting a tissue graft with an extraction composition that comprises an amphoteric detergent at a concentration, and for a contact time, that is sufficient to rupture cells in the tissue, and wherein the method is performed in the absence of an anionic detergent.

2. The method, according to claim 1, wherein after decellularization the extracellular matrix structures remain intact and preservation is measurably equal to or better than when decellularized by methods that include an anionic detergent.

3. The method, according to claim 1, wherein no anionic detergent is applied to the tissue.

4. The method, according to claim 1, wherein Triton X-200™ is not applied to the tissue.

5. The method, according to claim 1, wherein the concentration of the amphoteric detergent(s) is at least the critical micelle concentration.

6. The method, according to claim 1, wherein the extraction composition has physiologic, or greater, salinity.

7. The method, according to claim 1, further comprising physically removing non-structural debris from the tissue graft.

8. The method, according to claim 1, further comprising freezing the tissue graft either before or after decellurization.

9. The method, according to claim 1, further comprising introducing into the tissue graft one or more bioactive molecules or cells.

10. The method, according to claim 1, wherein the tissue graft's neurite-promoting activity is retained after decellularization compared to nerve tissue treated with buffer wash only.

11. The method, according to claim 1, wherein after decellularization the tissue graft's neurite-promoting activity is retained and preservation is measurably equal to or better than when decellularized by methods that include an anionic detergent.

12. The method, according to claim 1, wherein the amphoteric detergent is selected from the group consisting of sulfobetaine-10 (SB-10), sulfobetaine-16 (SB-16), and a combination thereof.

13. The method, according to claim 12, wherein the tissue graft is contacted with a first extraction composition consisting of SB-10 and then contacted with a second extraction composition consisting of SB-16.

14. The method, according to claim 1, further comprising at least one rinse step comprising contacting the tissue with a solution having less than physiologic salinity.

15. The method, according to claim 14, wherein the rinse solution has no salinity.

* * * * *